United States Patent [19]
Saadat et al.

[11] Patent Number: 6,139,570
[45] Date of Patent: Oct. 31, 2000

[54] DISPOSABLE BLADDER FOR INTRAUTERINE USE

[75] Inventors: Vahid Saadat, Sunnyvale, Calif.; Lee R. Bolduc, Ocala, Fla.

[73] Assignee: Gynelab Products, Inc., Ocala, Fla.

[21] Appl. No.: 08/858,133

[22] Filed: May 19, 1997

[51] Int. Cl.[7] ....................................................... A61F 7/00
[52] U.S. Cl. ........................................................... 607/105
[58] Field of Search ............................. 607/105, 96, 101, 607/102, 113, 156, 154

[56] References Cited

U.S. PATENT DOCUMENTS

| | | |
|---|---|---|
| 1,729,296 | 9/1929 | Sarason . |
| 2,168,427 | 8/1939 | McConkey . |
| 2,190,384 | 2/1940 | Newman ................................. 128/400 |
| 3,799,170 | 3/1974 | Walsh et al. . |
| 3,817,248 | 6/1974 | Buckles et al. . |
| 4,338,943 | 7/1982 | Okamoto et al. . |
| 4,823,812 | 4/1989 | Eshel et al. . |
| 4,949,718 | 8/1990 | Neuwirth et al. . |
| 5,105,808 | 4/1992 | Neuwirth et al. . |
| 5,159,925 | 11/1992 | Neuwirth et al. . |
| 5,197,457 | 3/1993 | Adair . |
| 5,248,312 | 9/1993 | Langberg . |
| 5,400,770 | 3/1995 | Nakao et al. . |
| 5,431,648 | 7/1995 | Lev ............................................ 606/27 |
| 5,433,708 | 7/1995 | Nichols et al. . |
| 5,501,681 | 3/1996 | Neuwirth et al. ......................... 606/21 |
| 5,507,732 | 4/1996 | McClure et al. . |
| 5,509,911 | 4/1996 | Cottone, Sr. et al. . |
| 5,509,929 | 4/1996 | Hascoet et al. ......................... 607/101 |
| 5,566,680 | 10/1996 | Urion et al. . |

Primary Examiner—Cary O'Connor
Assistant Examiner—Ryan Carter
Attorney, Agent, or Firm—Olson & Hierl, Ltd.

[57] ABSTRACT

A catheter device with disposable bladder is provided for intrauterine use and comprises a reusable introducer, a disposable bladder subassembly, a liquid source for pressurizing the bladder with a liquid, and a heater for heating the liquid enclosed within the bladder to a desired treatment temperature. The reusable introducer includes a catheter with a proximal end portion thereof carrying the heater. The disposable bladder subassembly includes a distendable balloon that terminates in a hollow, elongated rigid sleeve. A contact seal exists between the disposable balloon and the introducer. The device is especially well suited for effecting necrosis of substantially all of the tissue lining human uterus, and is specifically configured for intrauterine use.

32 Claims, 12 Drawing Sheets

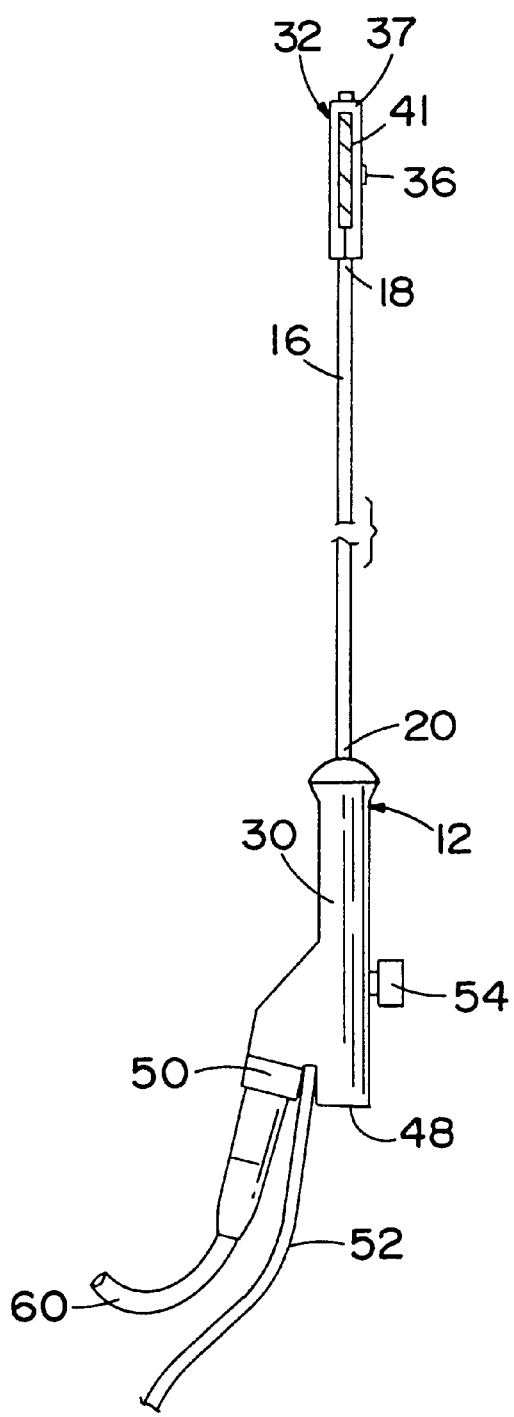
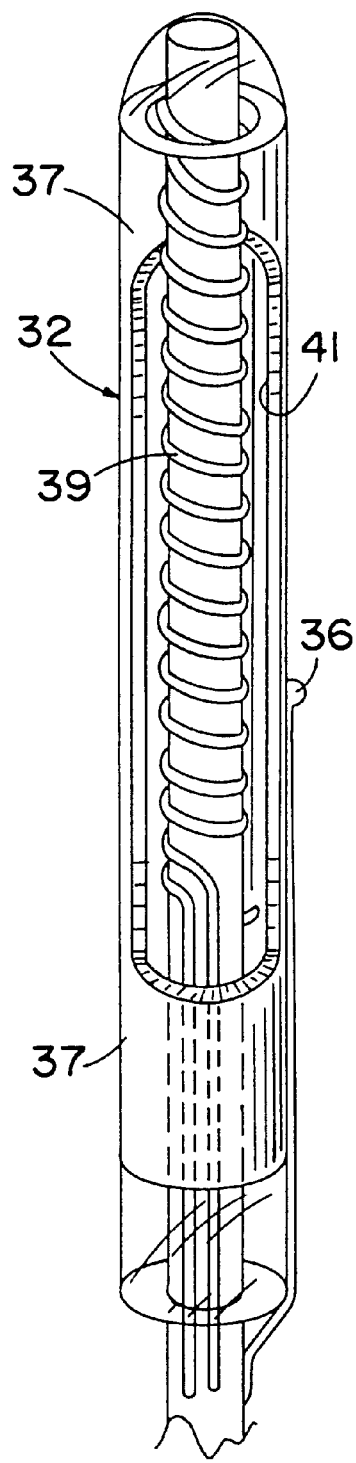
FIG. 5
FIG. 5A

DISPOSABLE BLADDER FOR INTRAUTERINE USE

TECHNICAL FIELD OF THE INVENTION

The invention relates to catheters for intrauterine use, and more particularly, to a disposable bladder subassembly for intrauterine devices.

BACKGROUND OF THE INVENTION

Removal of the uterine endometrium has proven an excellent alternative to a full hysterectomy in the surgical treatment of abnormal uterine bleeding, a symptom of menorrhagia. A variety of devices and associated techniques for endometrium removal are known. These include transcervical endometrial resection, ablation by laser treatment, ablation by electrosurgery, and thermal or cryogenic cauterization.

One highly successful intrauterine device for cauterization of the endometrium by thermal treatment is disclosed in the commonly owned U.S. Pat. No. 4,949,718 to Neuwirth et al., which is incorporated herein by reference to the extent pertinent. In the device disclosed in that patent, a distendable bladder made of an elastomeric material is mounted at one end portion of a catheter and encloses a heating element. Inserted into the uterus and distended with a liquid, the bladder expands to contact substantially all of the tissue that lines the human uterus, i.e. the uterine endometrium. A source of liquid under pressure, a heat source, and appropriate controls are provided to maintain pressure and temperature at the bladder and endometrium interface to effect necrosis.

Being safe, relatively faster, and less-likely to cause tissue damage to adjacent areas, the device discussed above compares well to the available alternatives. Despite its success, a major concern with such intrauterine devices as with all medical technology is cost. Sterility requirements often dictate that catheters either be fully disposable or in the alternative, durable enough to withstand rigorous thermal and chemical sterilization procedures. Therefore, one must either replace the catheter after each use or pay the extra cost required for highly durable materials as well as sterilization procedures. Until now, this constraint has undesirably contributed to the overall cost of surgical procedures employing intrauterine catheters, and the device discussed above in particular.

Efforts at reducing the overall costs of catheters while maintaining sterility are reflected in the development of disposable sheaths and introducers for reusable catheters. For example, U.S. Pat. No. 4,823,812 to Eshel et al. discloses a reusable rectal catheter for microwave treatment having a disposable jacket of elastomeric material with an integrally formed elastomeric balloon. Such disposable sheaths are ill suited to the intrauterine catheter described above, however, because the sheaths are flexible and subject to failure when used with pressurized fluids.

It would be desirable to provide an improved intrauterine catheter system having a disposable contact portion and a reusable portion substantially insulated from human body contact during use.

SUMMARY OF THE INVENTION

A catheter device having a reusable introducer and a disposable bladder subassembly is provided for intrauterine use. The device is specially suited for effecting necrosis of substantially all of the tissue lining a human uterus. Its modular design allows for the sterility required of an intrauterine catheter at a reduced cost because of a reusable portion and a coacting, comparably less expensive, disposable portion.

Specifically, this device includes a catheter having a rigid, closed distal end portion and a proximal end connected to a handle. A disposable and distendable balloon terminating in an elongated rigid sleeve is carried on the rigid distal end portion of the catheter and is sealingly held thereon. A contact seal exists between the disposable bladder subassembly and the introducer.

The catheter defines, at least in part, a liquid flow passageway (e.g. a lumen) to the distendable balloon. A liquid source for pressurizing and distending the balloon, typically a syringe, is connected to provide fluid communication with the flow passageway. A heater for heating the liquid used to distend the balloon is preferably positioned at the distal end of the catheter and is surrounded by the bladder.

The disposable bladder, including the balloon and the sleeve associated therewith, is dimensioned and configured for intrauterine use. The rigid sleeve is of sufficiently small diameter to pass through the cervix when the bladder is not distended. The outside surface of the rigid sleeve optionally carries a set of markings that serve as a depth gauge to indicate the depth of insertion. The distendable balloon is sized to contact substantially all of the endometrium that lines the uterine cavity.

BRIEF DESCRIPTION OF THE DRAWINGS

In the drawings,

FIG. 5 is a side view of the reusable introducer embodying the present invention;

FIG. 5A is an enlarged perspective view of the distal end portion of a reusable introducer embodying the present invention;

DESCRIPTION OF PREFERRED EMBODIMENTS

Figure 1:
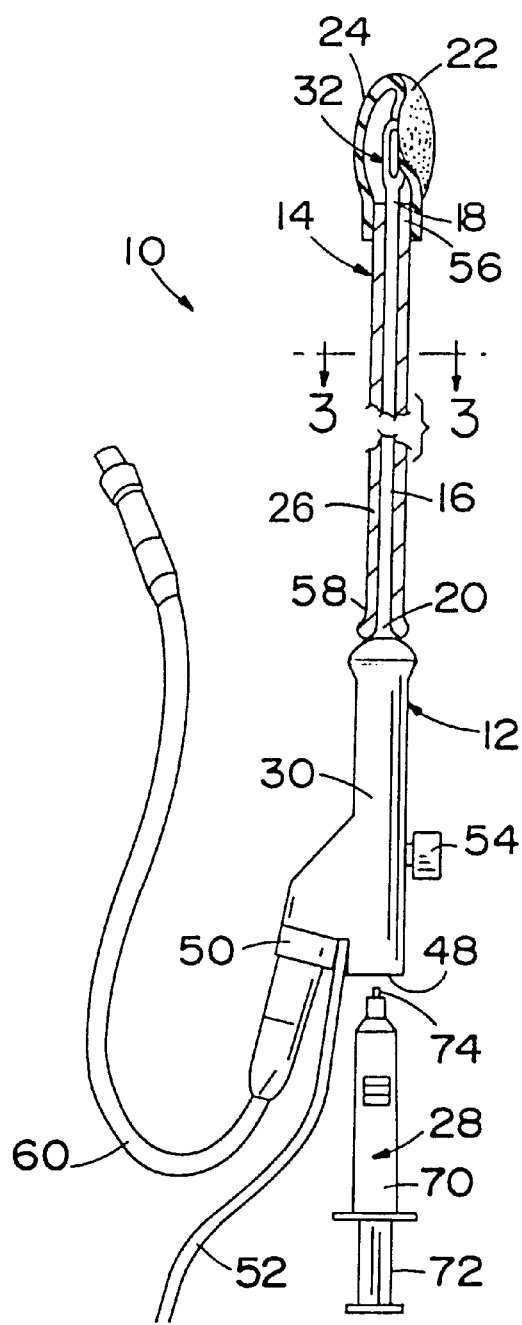
FIG. 1 is a side view of a catheter device embodying the present invention, partly in section to show interior details.
Figure 2:
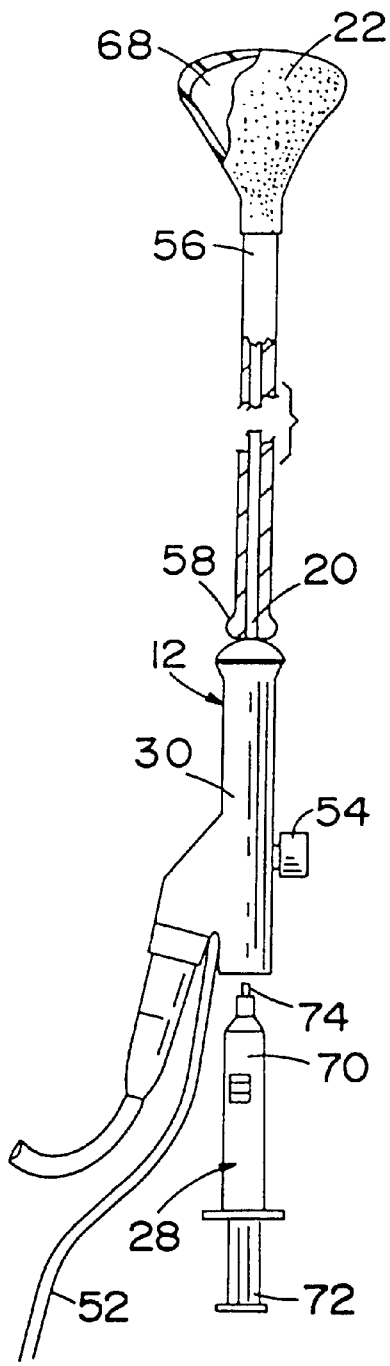
FIG. 2 is a side view of the catheter device of FIG. 1 but showing the distendable bladder in a distended configuration.

With reference to FIG. 1, catheter device 10 includes a reusable introducer 12 and a disposable bladder subassembly 14 slidably received by and sealingly held on introducer 12. Reusable introducer 12 includes a catheter 16 having a closed distal end portion 18 and a proximal end 20. Disposable bladder subassembly 14 includes a distendable balloon 22 mounted to a sleeve or hollow rigid stem 26. A liquid source 28 can be connected to catheter 16 through a handle manifold 30. A heater 32 is mounted on distal end portion 18 of catheter 16. Distendable balloon 22 defines an enclosure that is in communication with catheter 16 and can receive a distending liquid 68 from liquid source 28 (FIG. 2).

Preferably, distal end portion 18 carries heater 32 and defines at least one orifice for introducing a distending liquid into balloon 22 through one or more venting slots 41. One or more temperature sensors 36 (for example a thermocouple or thermistor) are positioned on heater housing 37. Catheter 16 defines passageways or lumens 38, 40 and 44 that provide communication between catheter proximal end 20 (which remains outside the patient) and distal end portion 18 (present inside the uterine cavity during treatment). If desired, the distending liquid 68 can be heated externally of the balloon 22.

Figure 3:
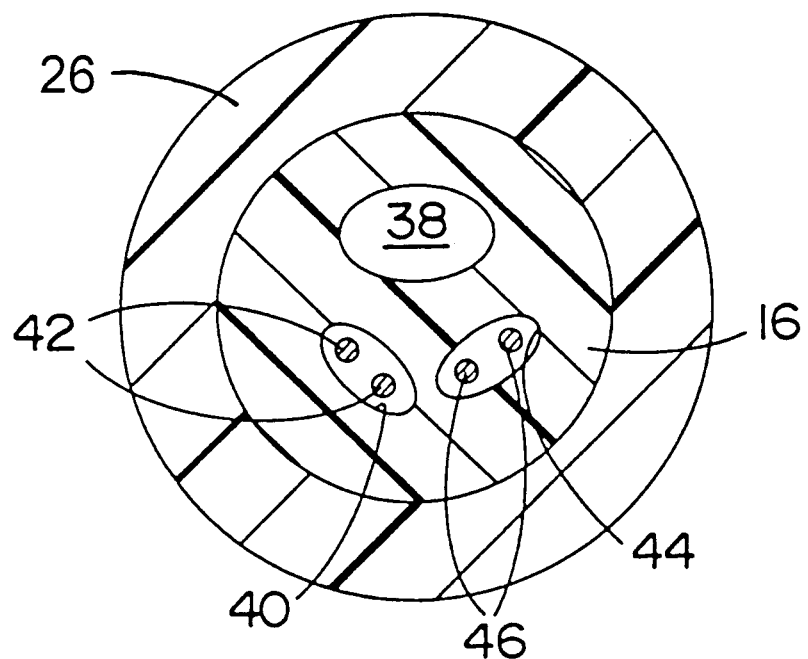
FIG. 3 is sectional view taken along plane 3—3 in FIG. 1.
Figure 4:
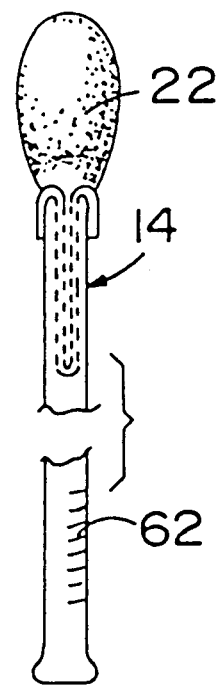
FIG. 4 is a side view of the disposable bladder subassembly embodying the present invention showing in phantom the distendable balloon in an optional storage position.

Referring to FIG. 3, three separate lumens are preferred: a liquid lumen (or liquid flow passageway) 38 to carry distending liquid into distendable balloon 22, a control signal lumen 40 to carry measurement signals including temperature sensor leads 42, and a heater power lumen 44 to carry electric power leads 46. If desired, signal lumen 40 and power lumen 44 can be combined into a single lumen.

Handle manifold 30 is secured to catheter proximal end 20, serves as an operator handle and also provides access ports to the various catheter lumens. Specifically, manifold 30 includes a fill port 48, a connector 50, and a pressure line 52. Fill port 48 communicates with lumen 38 to allow injection of distending liquid into distendable balloon 22. When open, a fill valve 54 links fill port 48 to lumen 38 to allow liquid injection, but seals fill port 48 when closed to maintain the desired pressure in distendable balloon 22. Via a control cable 60, connector 50 provides access by one or more control units (not shown) to the temperature sensor leads 42 and electric power leads 46. Also for connection to a control unit, pressure line 52 communicates a transducer (not shown) with lumen 38 to provide an indication of system pressure.

In the disposable bladder subassembly 14, sleeve 26 has a distal end 56 and a proximal end 58. Distendable balloon 22 is secured around rigid sleeve 26 at sleeve distal end 56. Distendable balloon 22, including its connection to rigid sleeve 26, must be capable of withstanding a temperature of at least about 125° C. without rupturing. In addition, distendable balloon 22 has heat transfer characteristics sufficient to provide efficient heating of tissue in contact therewith when distended. Material satisfactory for construction of distendable balloon 22 includes rubbers such as latex, silicone rubber, and the like. To provide the required durable seal, distendable balloon 22 is secured to sleeve 26 by an adhesive such as a cyanoacrylate adhesive, an epoxy adhesive, and the like.

FIG. 1 represents catheter device 10 as assembled with disposable bladder subassembly 14 sealingly held on catheter 16. Proximal end 58 of rigid sleeve 26 and open proximal end 20 of catheter 16 preferably are configured for interconnection to one another by a seal lock as will be discussed in detail hereinbelow. As shown in FIG. 1, sleeve 26 is sufficiently resilient to provide an interference fit and thus a liquid seal with catheter 16. Proximal end 58 can be configured to accommodate an elastomeric lining on its inner surface, if desired, to further enhance sealing.

As depicted in FIGS. 1 through 5A, liquid source 28 is typically a syringe having a barrel 70, a plunger 72, and a nozzle 74. Nozzle 74 and fill port 48 preferably have complementary interconnecting shapes, such as a luer type coupling. Liquid source 28 serves to expand and pressurize distendable balloon 22 by injection of a heat transfer liquid through liquid lumen 38 and into distendable balloon 22. Heat transfer liquid is preferably a sterile non-toxic liquid with a boiling point of at least 212° F. (110° C.). A five percent dextrose in water solution has proven satisfactory for this purpose. When distended, balloon 22 preferably assumes a pyriform configuration as shown in FIG. 2.

Heater 32, typically a resistive coil 39, is carried by distal end portion 18 of catheter 16, and is positioned within bladder enclosure 24. Electric power leads 46 connect to heater 32, providing power and remote control. Heater housing 37 is equipped with elongated venting slot 41 and protects distendable balloon 22 from directly contacting heater 32. When energized, heater 32 raises the temperature of the liquid within distendable balloon 22 to a desired temperature for the intended necrosing treatment.

Disposable bladder subassembly 14 and catheter 16 are specifically configured in both dimension and material to be received within the human uterus through the cervix when distendable balloon 22 is in its relaxed state, i.e., not distended. The size of sleeve 26 is selected to allow its insertion into a partially dilated cervix. The outside diameter of sleeve 26 preferably is not more than about 5 millimeters. To allow interconnection, the inside diameter of sleeve 26 is dictated by the outside diameter of catheter 16.

To aid the physician in inserting catheter device 10 into the uterus, the exterior surface of sleeve 26 optionally includes scaled position markings 62 that indicate depth of insertion. Sleeve 26 can be opaque or transparent, as desired. If sleeve 26 is transparent, the scaled position markings can be placed on catheter 16. Catheter 16 is about 20 centimeters long, and the distendable balloon 22 is about 4 centimeters to about 5 centimeters long. The length of sleeve 26 depends upon the coupling mechanism utilized to retain sleeve 26 on catheter 16.

The combination of sleeve 26 and catheter 16 must be sufficiently rigid or stiff to facilitate insertion and to provide tactile feedback as catheter device 10 is positioned in the uterine cavity, thereby reducing the risk of uterine perforation. The flexibility of rigid sleeve 26 preferably does not exceed a Shore Hardness value of about 50 A. Rigid sleeve 26 is preferably formed of a rigid plastic material that is temperature resistant within the operating temperature range such as polyurethane, nylon, or the like. Rigid sleeve 26 can be made of an insulating material as well.

Catheter 16 and handle manifold 30 may be formed of various metallic and non-metallic, e.g., plastic, materials of varying rigidity. Without intending any limitation, suitable non-metallic materials include acrylonitrile-butadiene-styrene (ABS) copolymers, polycarbonates, polyurethanes, and the like. A polyurethane is preferred for catheter 16 and an ABS copolymer is preferred for handle manifold 30. Among metallic materials of construction, stainless steel is preferred.

Figure 6:
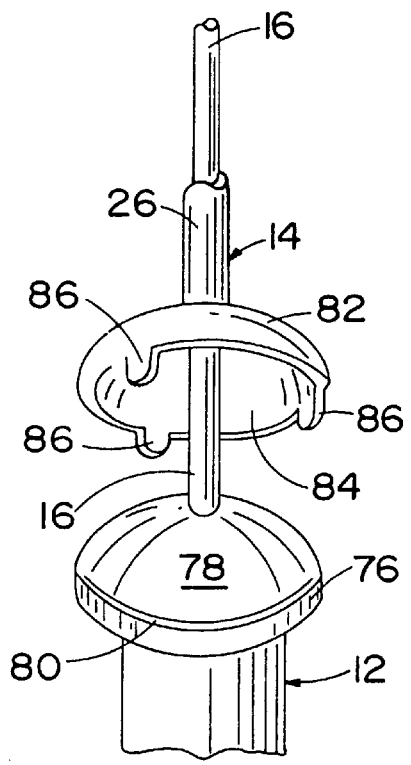
FIG. 6 is a fragmentary perspective view showing a snap-fit type seal lock for interconnecting disposable and reusable portions of a catheter device embodying the present invention.

To further enhance the connection between rigid sleeve 26 and catheter 16, a seal lock in the form of various coupling mechanisms including elastomeric linings may be provided. As illustrated in FIG. 6, a snap-fit coupling may serve as a seal lock between rigid sleeve 26 and catheter 16. The snap-fit coupling in FIG. 6 comprises a convex fitting 76 on catheter 16 having an exposed surface 78 with an elastomeric lining 80 and a receptacle fitting 82 on rigid sleeve 26 defining a concave surface 84 complementary to exposed surface 78. Receptacle fitting 82 has spaced latch fingers 86 about the periphery of receptacle fitting 82 to engage convex fitting 76.

Figure 7:
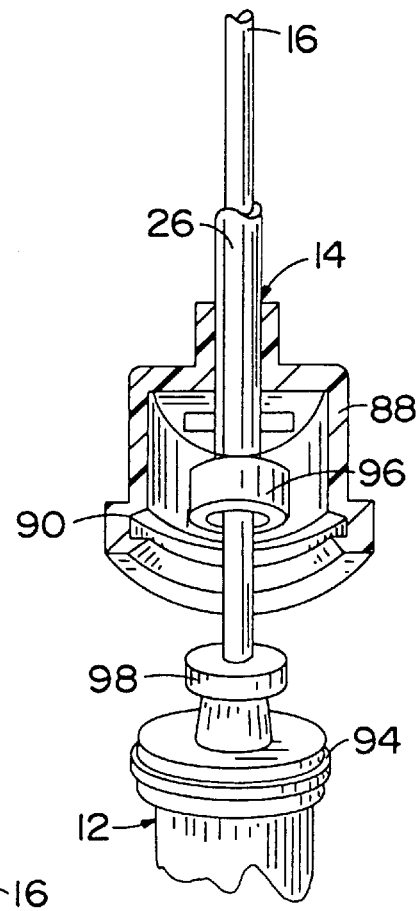
FIG. 7 is a fragmentary perspective view showing another snap-fit type seal lock for interconnecting disposable and reusable portions of a catheter device embodying the present invention, partly in section to show interior details.

FIG. 7 illustrates an alternate snap-fit coupling that forms a seal lock between rigid sleeve 26 and catheter 16. The snap-fit coupling shown in FIG. 7 includes a cup 88 extending circumferentially around rigid sleeve 26 with a radial groove 90 on its inside surface to engage a raised snap collar 94. Snap collar 94 and cup 88 when engaged serve to enclose and urge together a proximal flange 96 and raised seat collar 98.

Figure 8:
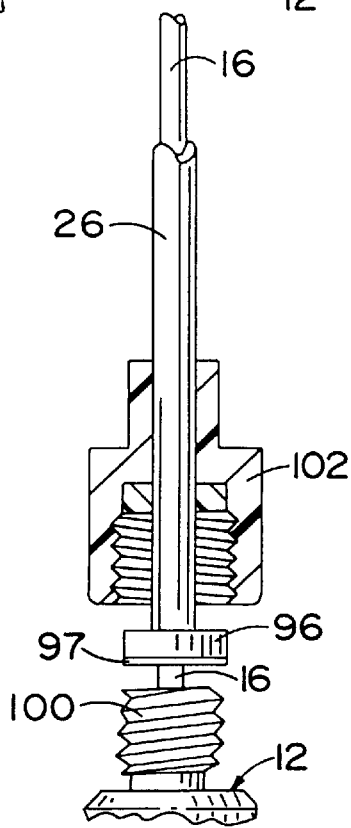
FIG. 8 is a fragmentary side view showing seal lock by threaded fittings for interconnection, partly in section to show interior details.

Referring now to FIG. 8, a threaded coupling can also serve as a seal lock. It comprises an externally threaded fitting 100 on catheter 16 and a threaded cap 102 rotatably mounted on rigid sleeve 26. A proximal flange 96 serves as a mechanical stop for threaded cap 102, and includes an elastomeric lining 97.

Figure 9:
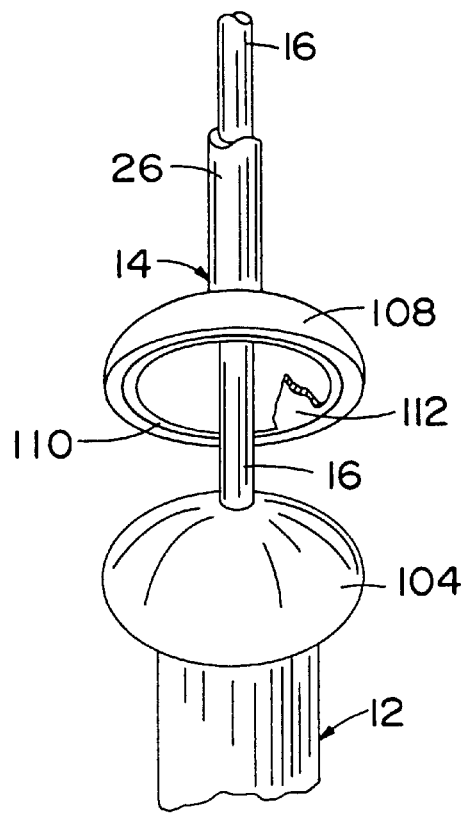
FIG. 9 is a fragmentary perspective view showing a magnetic-coupling type seal lock for interconnection.
Figure 10:
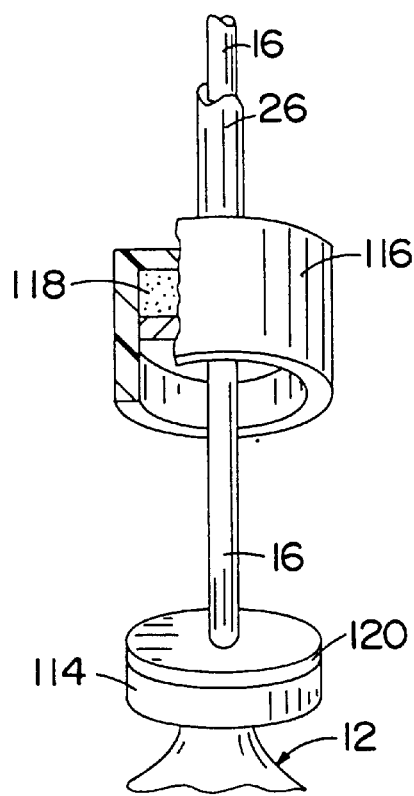
FIG. 10 is a fragmentary perspective view showing another magnetic-coupling type seal lock for interconnection, partly in section to show interior details.

FIGS. 9 and 10 illustrate alternate, magnetic couplings. The magnetic coupling shown in FIG. 9 includes a male fitting 104 of a rare-earth magnet material on catheter 16 and a receptacle fitting 108 formed of magnetizable material on rigid sleeve 26. An elastomeric lining 110 covers a concave mating surface 112 of receptacle fitting 108 to ensure sealed interconnection. The magnetic coupling depicted in FIG. 10 comprises a magnetizable washer 114 secured around catheter 16 and a cylindrical receptacle fitting 116 that includes a rare-earth magnet 118. The washer surface has an elastomeric lining 120 for improved seal action.

Figure 11:
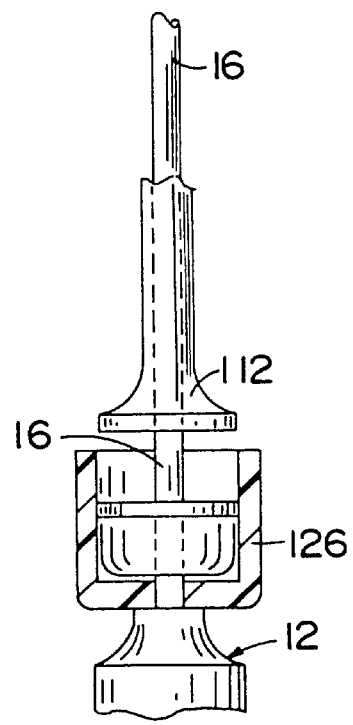
FIG. 11 is a fragmentary side view showing yet another magnetic-coupling type seal lock for interconnection, partly in section to show interior details.

FIG. 11 represents another suitable magnetic coupling. Here, a magnetizable washer is mounted on rigid sleeve 26 and a magnetic fitting 124 is mounted on catheter 16. A housing 126 is provided to enclose magnetizable washer and magnetic fitting 124.

Figure 12:
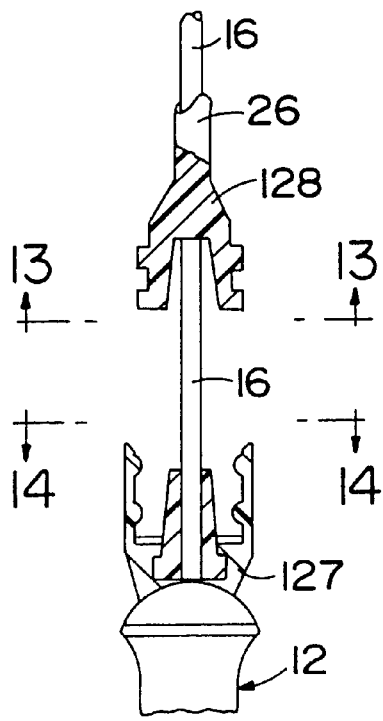
FIG. 12 is a fragmentary side view showing a locking luer type seal lock for interconnection, partly in section to show interior details.
Figure 13:
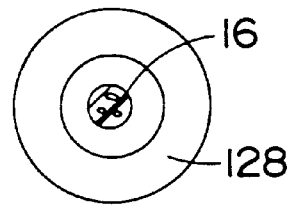
FIG. 13 is a sectional view taken along plane 13—13 in FIG. 12.
Figure 14:
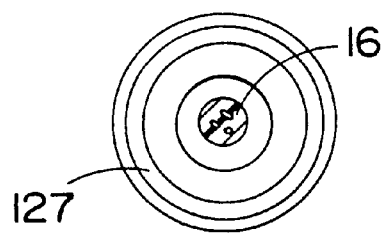
FIG. 14 is a sectional view taken along plane 14—14 in FIG. 12.

Given their wide-spread use in medical devices, luer couplings can be configured to link rigid sleeve 26 to catheter 16, as shown in FIG. 12. In the illustrated embodiment, a male luer fitting 127 is secured on catheter 16 and a female luer fitting 128 is mounted on rigid sleeve 26. When engaged male luer fitting 127 and female luer fitting 128 form a seal in the conventional fashion. Although a locking luer coupling is illustrated, a friction-fit coupling is also suitable. Rigid sleeve 26 may be shaped so that a female luer fitting is an integral part thereof.

Figure 15:
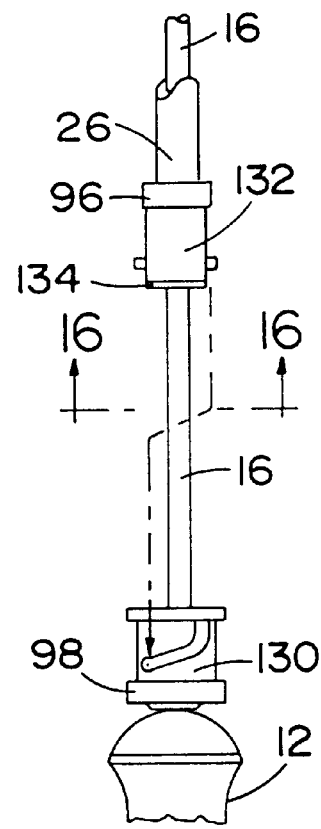
FIG. 15 is a fragmentary side view showing a bayonet-fitting type seal lock for interconnection.
Figure 16:
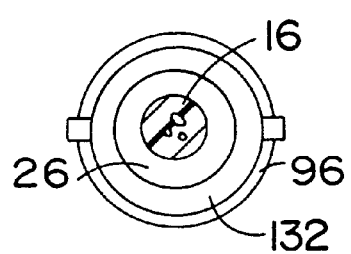
FIG. 16 is a sectional view taken along plane 16—16 in FIG. 15.

As illustrated in FIGS. 15 and 16, a bayonet coupling may also serve to form a seal lock between rigid sleeve 26 and catheter 16. The bayonet coupling comprises a female bayonet fitting 130 on catheter 16 abutting seat collar 98 and a male bayonet fitting 132 on rigid sleeve 26 abutting proximal flange 96. Male bayonet fitting 132 preferably includes an elastomeric lining 134, which optionally extends to the inside surface of rigid sleeve 26 to ensure a sealed connection.

FIGS. 17–23 illustrate an alternate embodiment of the present invention in which the liquid source is connected to the catheter through an access port in the rigid sleeve of the disposable bladder subassembly. Within FIGS. 17 through 23 structural elements performing a similar function to elements previously shown in FIGS. 1 through 5 generally have the same last two digits in their reference numerals.

Figure 17:
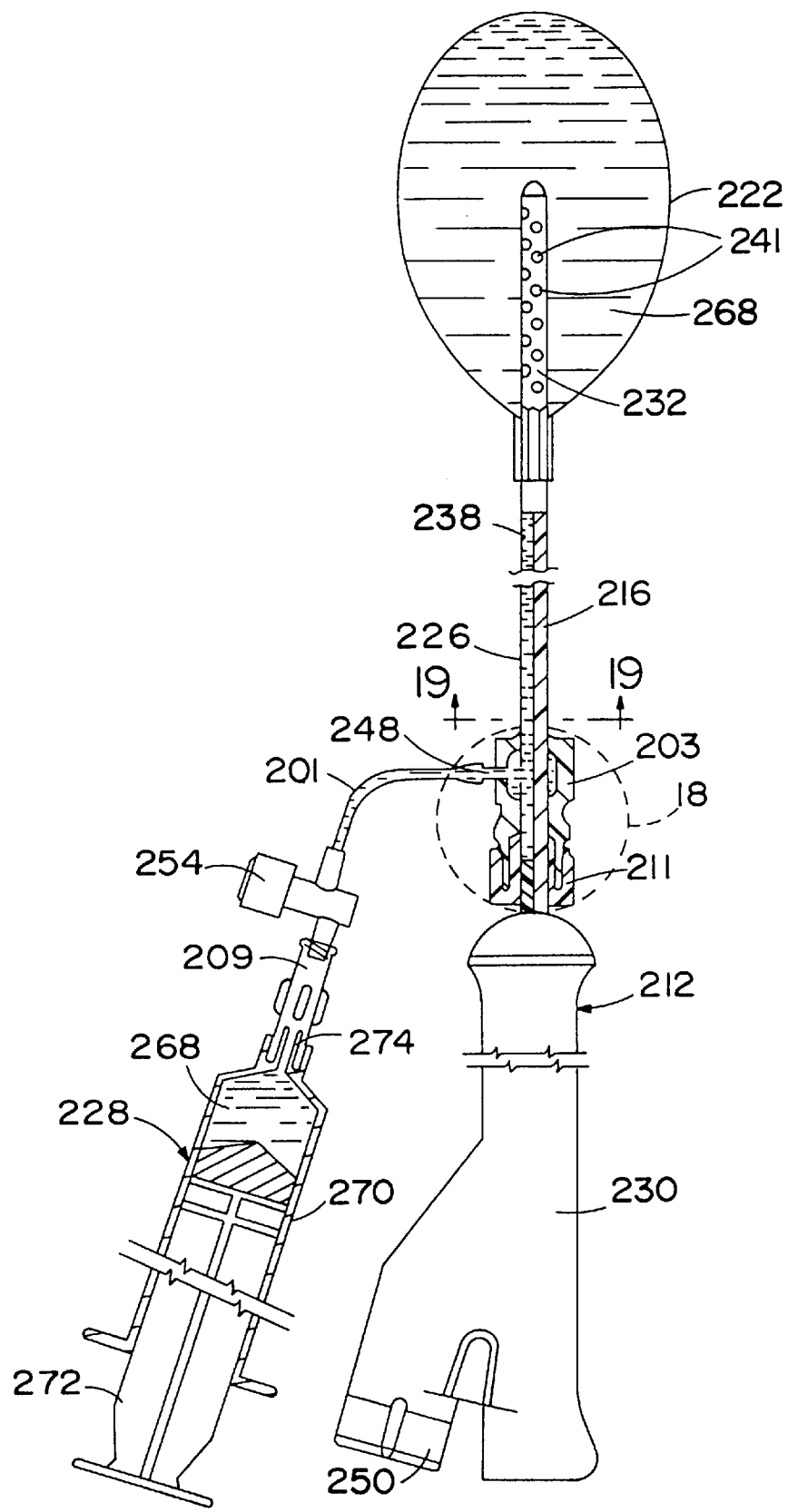
FIG. 17 is a side view of a catheter device according to another embodiment of the present invention, partly in section to show interior details.
Figure 18:
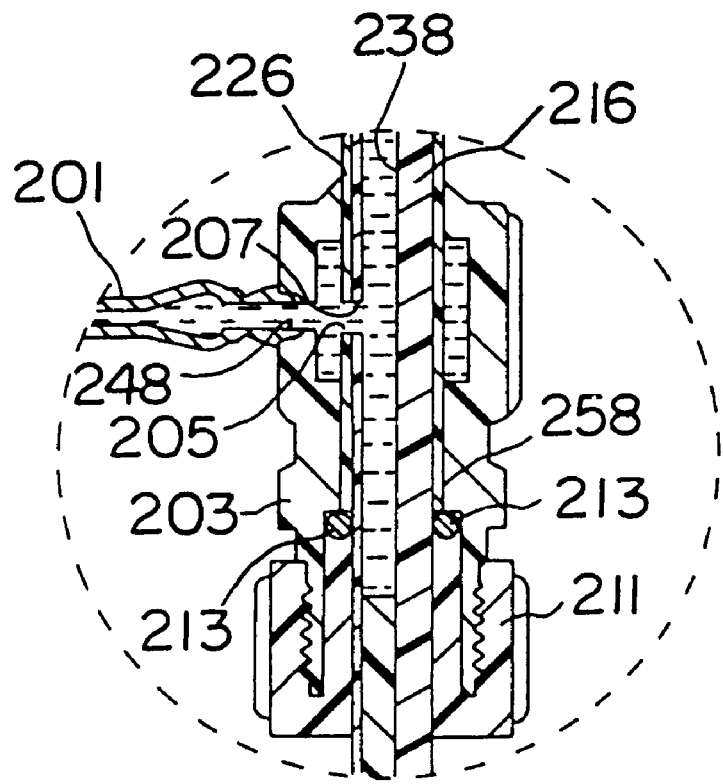
FIG. 18 is an enlarged view of the portion of FIG. 17 within circle 17.
Figure 19:
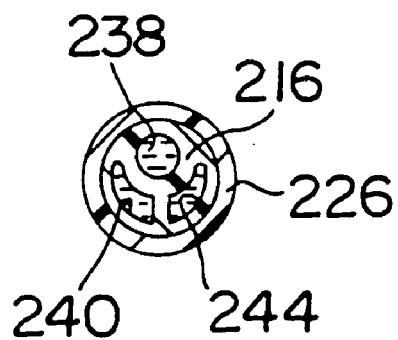
FIG. 19 is a sectional view taken along plane 20—20 in FIG. 18.

FIG. 17 shows a liquid source 228 connected to catheter 216 through fill valve 254, liquid line 201, and fill port 248 in threaded fitting 203. A liquid access opening 205 in rigid sleeve 226 and an opening 207 in catheter 216 allow distending liquid 268 to flow from fill port 248 into liquid lumen 238 and on to distendable balloon 222. When open, fill valve 254 links liquid source 228 to fill port 248, but seals liquid source 228 when closed to maintain the desired pressure in distendable balloon 222.

Liquid source 228, a syringe, includes a barrel 270, a plunger 272, and a nozzle 274. An adapter 209 interconnects nozzle 274 and fill valve 254. While adapter 209 allows for interconnection of conventional valve and syringe components, numerous various are of course possible. For example, fill valve 254 and liquid source 228 could be integrated into a single component. If desired, liquid source 228 could be clipped or somehow secured to handle 230 to aid handling by the physician.

Figure 20:
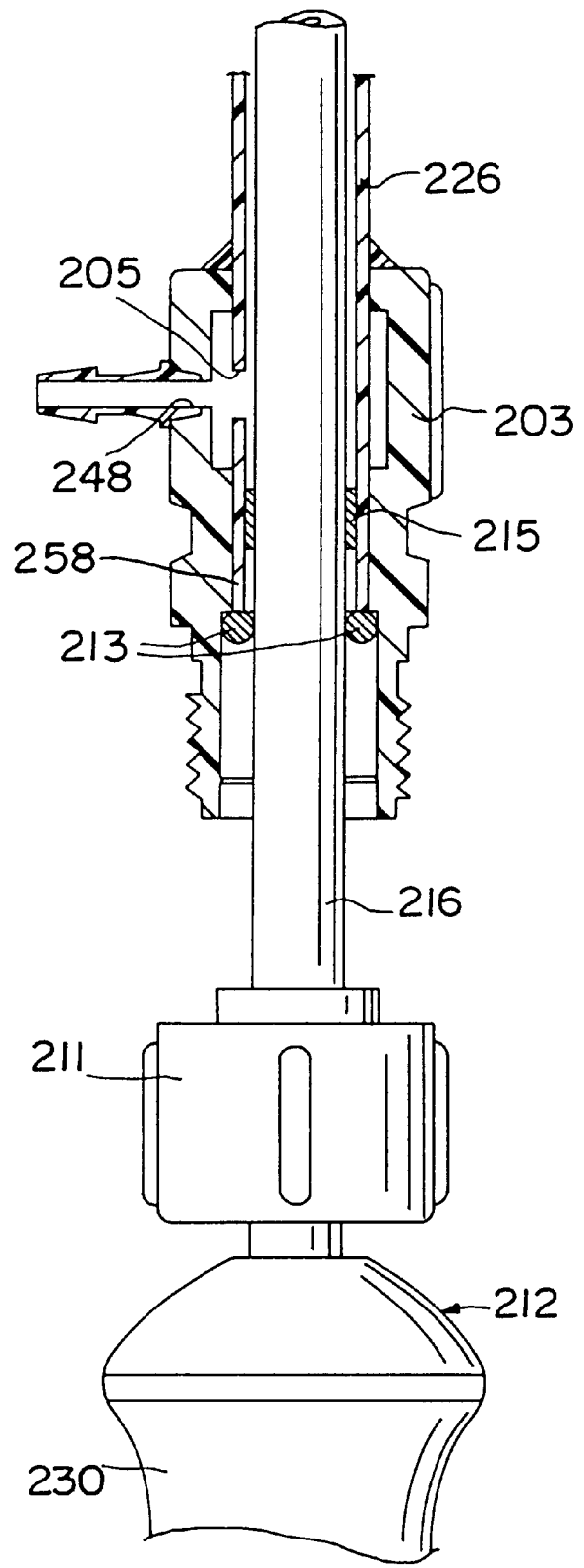
FIG. 20 is a fragmentary side view, partly in section to show interior detail, showing a seal lock by threaded coupling for interconnecting disposable and reusable portions of a catheter device embodying the present invention.

As best illustrated in FIG. 20, a seal lock in the form of a threaded coupling enhances the connection between rigid sleeve 226 and catheter 216. Threaded fitting 203 is secured around rigid sleeve 226 at proximal end 258. A threaded cap 211 is rotatably mounted on catheter 216 to receive threaded fitting 203. An elastomeric ring 213 is positioned between threaded fitting 203 and threaded cap 211. To further enhance the seal between catheter 216 and sleeve 226, the inner surface of rigid sleeve 226 includes an elastomeric lining 215.

Figure 21:
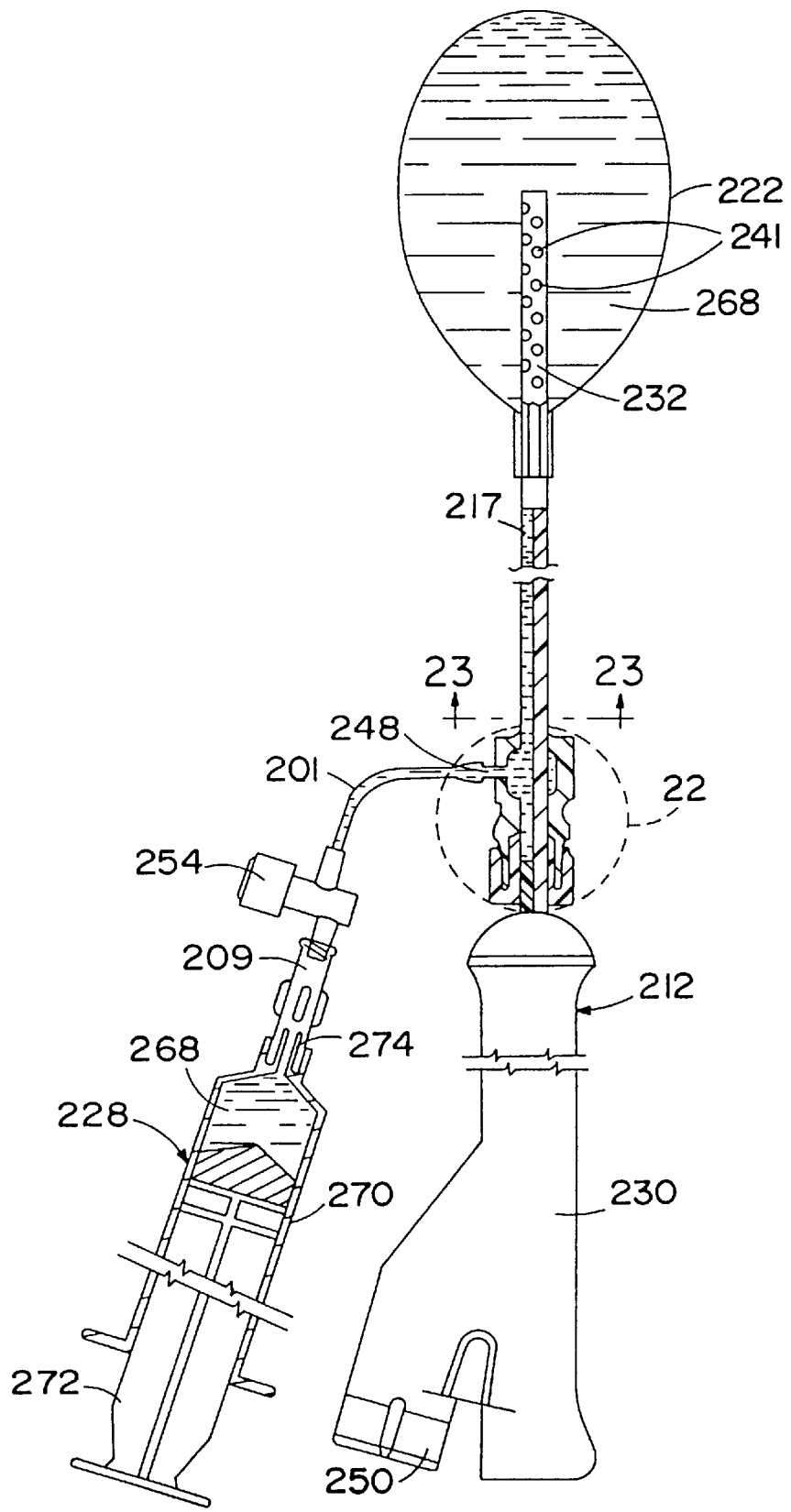
FIG. 21 is a side view of a catheter device according to yet another embodiment of the present invention, where a liquid passageway is defined by a groove in the introdcuer together with the sleeve of the disposable bladder subassembly.
Figure 22:
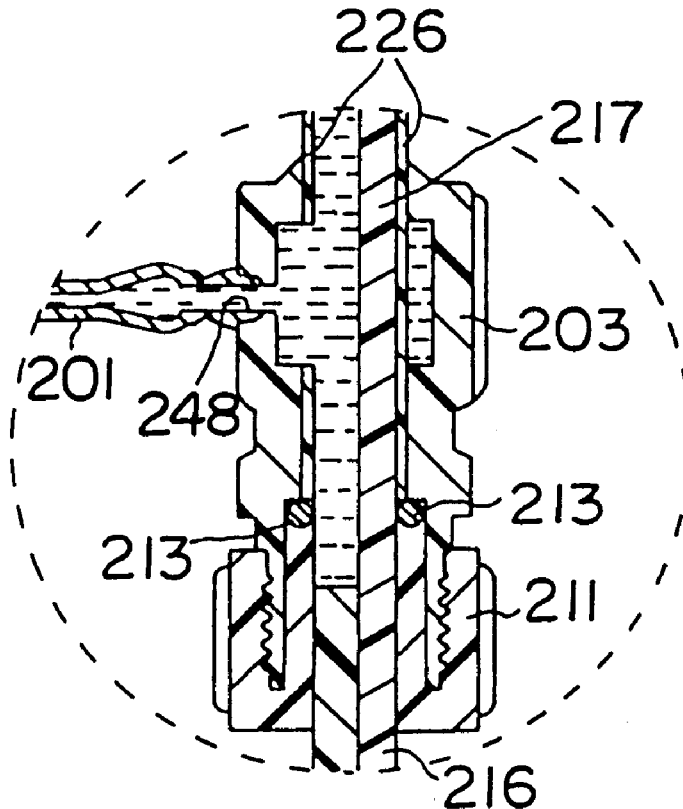
FIG. 22 is an enlarged view of the portion of FIG. 21 within circle 22.
Figure 23:
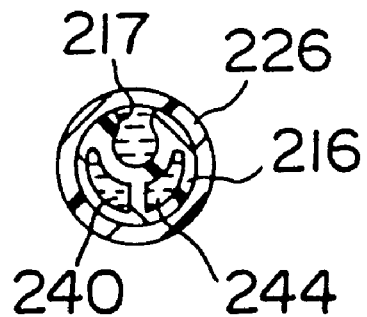
FIG. 23 is a sectional view taken along plane 23—23 in FIG. 21.

As illustrated in FIGS. 21 through 23, a groove 217 in catheter 216, when enclosed by rigid sleeve 226, can serve as the flow passageway for distending liquid 268. Such a groove configuration allows for easier cleaning of catheter 216. When distendable balloon 222 is filled, distending liquid 268 flows from fluid source 228 through adapter 209, fill valve 254, and liquid line 201, to fill port 248 in threaded fitting 203. From fill port 248, distending liquid 268 next flows past sleeve 226 and into the passageway formed by groove 217 and sleeve 226. Distending fluid then flows through this passageway and on to the closed distal end portion 218 of catheter 16, where at least one orifice opening allows the fluid to enter the enclosure formed by distendable balloon 222.

Devices constructed embodying the present invention exhibit a series of advantageous features. For example, disposable bladder subassembly 14 can be stored and dispensed in a highly protective configuration with distendable balloon 22 drawn within hollow sleeve 26, as shown in phantom in FIG. 4 and in FIGS. 24 and 25. A further advantage of the present invention is its modular construction which allows the body contact portion, here disposable bladder subassembly 14, to be discarded while the more expensive introducer 12 can be reused.

Figure 24:
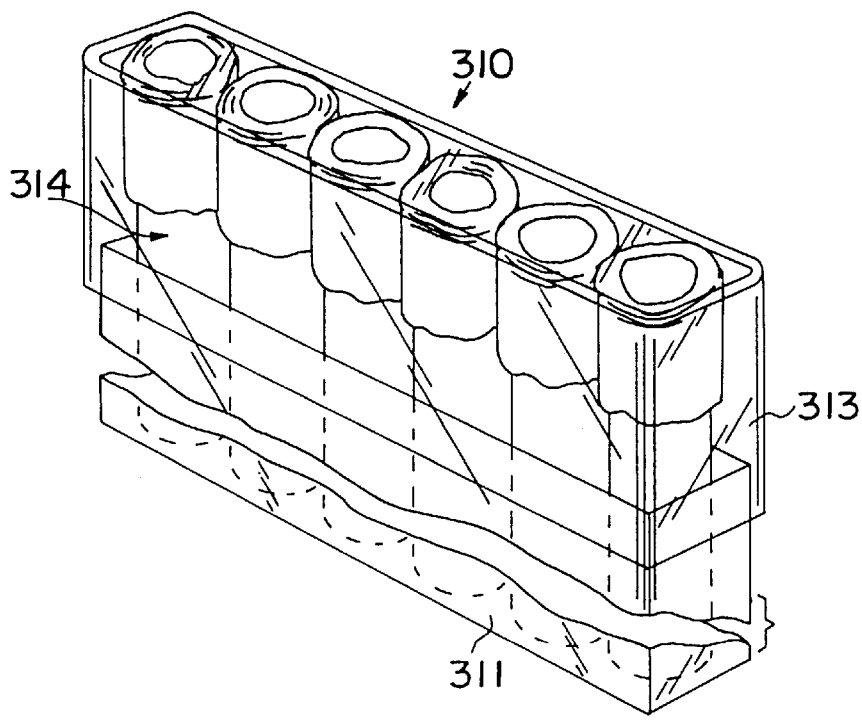
FIG. 24 is a perspective view of a packaged array of disposable bladders embodying the present invention.

The disposable bladder subassemblies embodying the present invention can be packaged as an array of two or more subassemblies. An illustrative packaged array of six disposable bladder subassemblies is shown in FIG. 24. Packaged array 310 includes six disposable bladder subassemblies such as subassembly 314 contained in box 311 provided with a transparent cover 313 or the like. As shown in greater detail in FIG. 25, disposable bladder subassembly 314 includes hollow stem 326, which defines a through passageway 315, and distendable balloon 322 attached to one end of stem 326. If desired, stem 326 can be made of an insulating material, i.e., a material of relatively low thermal conductivity to minimize undesirable heat transfer to tissue in contact therewith. During storage in box 311, distendable balloon 322 is removably situated within the passageway 315 defined by stem 326.

Figures 25, 26:
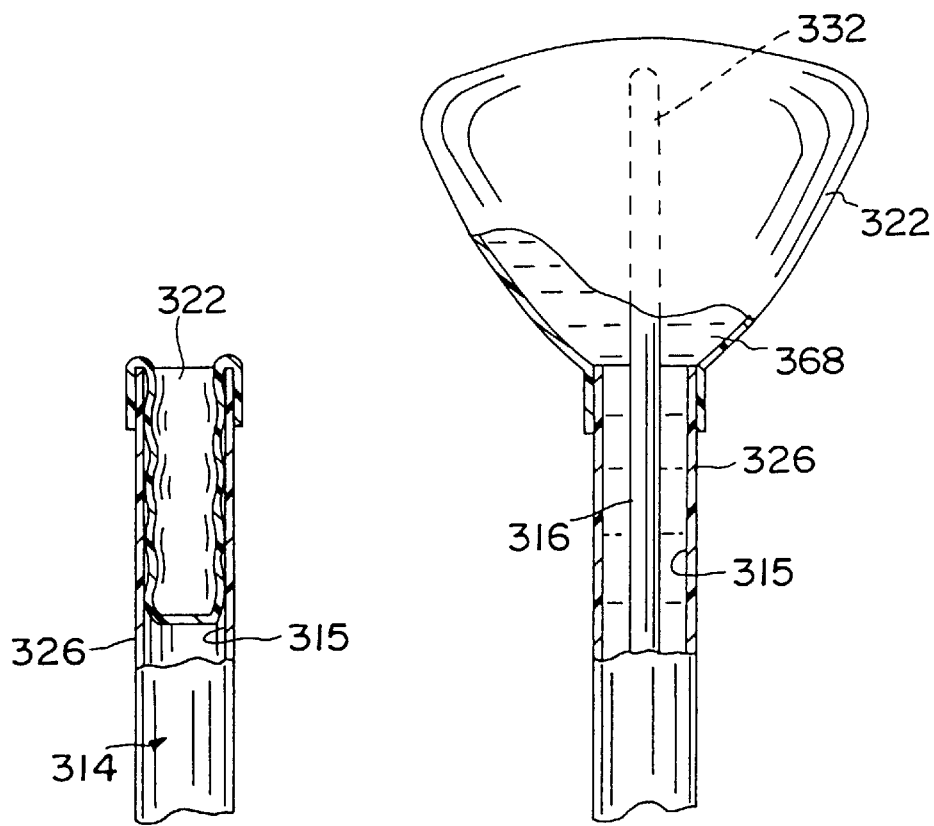
FIG. 25 is an enlarged, side elevational view, partly in section to show interior detail, depicting a disposable bladder subassembly having a distendable elastomeric balloon situated within an elongated hollow sleeve.
FIG. 26 is an enlarged, fragmentary side view, partly in section to show interior detail, and depicting the distendable balloon of FIG. 25 in its distended configuration when positioned within the uterine cavity.

FIG. 26 shows disposable bladder subassembly 314 mounted to an introducer which includes catheter 316 carrying heater 332. Distendable balloon 322 is shown in a distended state and having assumed a substantially pyriform, i.e., pear shaped, configuration so that contact is made with substantially all of the endometrium lining a human uterus. Distendable balloon 322 is distended by a liquid 368 introduced through catheter 316 and heated by heater 332. Distendable balloon 322 is pushed out of the storage position shown in FIG. 25 as the disposable bladder subassembly 314 is mounted to the introducer.

In use, the patient's cervix of the uterus is slightly dilated to provide an opening about 5 millimeters in diameter. The end of a catheter bearing the bladder in a collapsed state is then slowly inserted through the cervical ostium into the uterine cavity until the surgeon feels the tip of the rigid proximal end portion touch the fundus of the uterus. At this stage of the treatment, tactile feedback becomes a feature of the device to ensure proper insertion.

After insertion, the distendable balloon of the disposable bladder subassembly is then inflated with a heat transfer liquid until a pressure sufficient to compress the tissue contiguous to the balloon is attained. In this manner applied pressure reduces blood flow to the compressed tissue and thereby reduces any counteracting cooling effect provided by circulating blood. The heat transfer liquid is heated by the heating element within the balloon to a temperature sufficient to maintain the balloon exterior at a desired predetermined temperature. The heating is continued for a time period necessary to effect cauterization of the endometrium in its entirety, usually about 8 to 10 minutes.

At the conclusion of the medical procedure, heating is discontinued, the heat transfer liquid is withdrawn from the balloon, thereby collapsing the balloon, and the device is thereafter withdrawn from the patient.

We claim:

1. A device for effecting necrosis of substantially all of the tissue lining a human uterus, which device includes:

an introducer comprising a catheter for insertion into the human uterus, said catheter defining at least in part a liquid flow passageway and having a rigid, closed distal end portion;

a removable balloon subassembly, having a distendable balloon defining an enclosure in communication with said passageway and terminating in a rigid sleeve sealingly held on and removably secured to said rigid, closed distal end portion of said catheter, said balloon being secured to a distal end of said sleeve and projecting axially beyond the distal end of the catheter when distended, and being distendable to contact substantially all of the tissue lining the human uterus;

a source of liquid in fluid communication with said passageway for distending said balloon with a liquid; and a heater for heating said liquid.

2. The device according to claim 1 wherein said liquid flow passageway is a lumen in said catheter.

3. The device according to claim 1 wherein said liquid flow passageway is defined by a groove formed in the material of said catheter together with said rigid sleeve.

4. The device according to claim 1 wherein said liquid flow passageway and said source of liquid are operably connected through a liquid access opening formed in the material of said rigid sleeve.

5. The device according to claim 1 wherein said catheter has an open proximal end in liquid flow communication with said source of liquid.

6. The device according to claim 1 wherein said rigid sleeve is dimensioned to pass through the cervical ostium.

7. The device according to claim 1 wherein said rigid sleeve and said removable bladder subassembly substantially are dimensioned to fit through the cervical ostium when said balloon is not distended.

8. The device according to claim 1 wherein said rigid sleeve has an outer surface with scaled position markings that indicate depth of insertion.

9. The device according to claim 1 wherein said rigid sleeve is sealingly held on said rigid, closed distal end portion by a seal lock between said rigid sleeve and said catheter.

10. The device according to claim 9 wherein said rigid sleeve has a distal end carrying said balloon and a proximal end, the proximal end of said rigid sleeve is enlarged, and said seal lock comprises an elastomeric lining on the inner surface of the proximal end of said rigid sleeve.

11. The device according to claim 9 wherein said seal lock is a compression fitting on said catheter, said compression fitting is provided with an elastomeric lining and urges the elastomeric lining against said catheter.

12. The device according to claim 9 wherein said rigid sleeve has a proximal flange with an elastomeric lining and said catheter has a corresponding raised seat collar abutting said proximal flange.

13. The device according to claim 12 wherein said seal lock is a threaded coupling comprising:

an externally threaded fitting on said catheter;

a threaded cap rotatably mounted on said rigid sleeve and abutting said proximal flange; and an elastomeric layer therebetween.

14. The device according to claim 9 wherein said seal lock is a bayonet coupling comprising:

a female bayonet fitting on said catheter;

a male bayonet fitting on said rigid sleeve; and an elastomeric layer therebetween.

15. The device according to claim 9 wherein said seal lock is a snap-fit coupling comprising;

a cup extending circumferentially around said rigid sleeve, lined with an elastomeric material and having a radial groove on an inside surface facing said rigid sleeve; and a raised snap collar dimensioned to engage said radial groove.

16. The device according to claim 9 wherein said seal lock is a magnetic coupling comprising:

a male fitting of rare-earth magnet material on said catheter; and a receptacle fitting of magnetizable material on said rigid sleeve, said receptacle fitting having a mating surface; and an elastomeric lining on said mating surface.

17. The device according to claim 16 wherein said male fitting has a convex mating surface and said receptacle fitting has a mating surface complementary thereto.

18. The device according to claim 1 wherein said rigid sleeve is sealingly held on said rigid, closed distal end portion by a luer coupling comprising:

a male luer fitting secured on said catheter; and a female luer fitting on said rigid sleeve, said luer coupling forming a seal between said catheter and said rigid sleeve.

19. The device according to claim 18 wherein said luer coupling is a friction-fit luer coupling.

20. The device according to claim 18 wherein said luer coupling is a locking luer coupling.

21. The device according to claim 18 wherein said female luer fitting is integral with said rigid sleeve.

22. The device according to claim 1 wherein said rigid sleeve is sealingly held on said rigid, closed distal end portion by a snap-fit coupling comprising:

a convex fitting having an exposed surface with an elastomeric lining on said catheter; and a receptacle fitting on said rigid sleeve defining a concave surface complementary to said exposed surface, said receptacle having spaced latch fingers about the periphery of said receptacle to engage said convex fitting.

23. The device according to claim 1 wherein said rigid sleeve is sealingly held on said rigid, closed distal end portion by a threaded coupling comprising:

a threaded cap rotatably mounted on said catheter; and a threaded fitting on said rigid sleeve.

24. The device according to claim 23 wherein said threaded fitting includes a liquid access port, said liquid access port being in fluid communication with said liquid flow passageway.

25. A removable bladder subassembly for intrauterine use with a catheter having a distal end portion, said subassembly comprising:

a distendable balloon terminating in a rigid sleeve attached to the balloon and having a proximal end portion; and a connector fitting on the proximal end portion of said rigid sleeve for removable securement of said rigid sleeve to said distal end portion of said catheter.

26. A disposable bladder subassembly for an intrauterine catheter device, said disposable bladder subassembly comprising:

a distendable enclosure attached to one end of a hollow rigid stem that defines a passageway, said rigid stem having an open opposite end and said enclosure being in communication with said open opposite end through said passageway; and a connector coupling at the open opposite end of said hollow rigid stem for removably connecting and sealing said hollow rigid stem to the catheter device.

27. The disposable bladder subassembly according to claim 26 wherein said connector coupling includes an elastomeric seal.

28. The disposable bladder subassembly according to claim 27 wherein said connector coupling includes an inner surface and said elastomeric seal is an elastomeric lining on said inner surface of said connector coupling.

29. The disposable bladder subassembly according to claim 26 wherein said distendable enclosure is positioned within said rigid stem, whereby said distendable enclosure is protected from damage before use.

30. A packaged array of disposable bladder subassemblies suitable for removable attachment to the distal end portion of a catheter suitable for intrauterine use, each disposable bladder subassembly in said array comprising:

a distendable balloon defining an enclosure; and a hollow stem attached to the balloon at one end and adapted to be removably secured to the distal end portion of the catheter and defining a through passageway in communication with an enclosure defined by the distendable balloon.

31. The packaged array according to claim 30 wherein the distendable balloon is removably situated within the hollow stem.

32. The packaged array according to claim 30 wherein the hollow stem is made of a material having a relatively low thermal conductivity.

* * * * *